(12) United States Patent
Wang et al.

(10) Patent No.: US 11,450,424 B2
(45) Date of Patent: Sep. 20, 2022

(54) TRAINING FRAMEWORK FOR MULTI-GROUP ELECTROCARDIOGRAPHY (MG-ECG) ANALYSIS

(71) Applicant: TENCENT AMERICA LLC, Palo Alto, CA (US)

(72) Inventors: Kun Wang, San Jose, CA (US); Tao Yang, Mountain View, CA (US); Min Tu, Cupertino, CA (US); Yaliang Li, Santa Clara, CA (US); Hui Tang, Mountain View, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 280 days.

(21) Appl. No.: 16/556,491

(22) Filed: Aug. 30, 2019

(65) Prior Publication Data

US 2021/0065876 A1    Mar. 4, 2021

(51) Int. Cl.
*G16H 30/20*       (2018.01)
*G06N 20/00*       (2019.01)

(52) U.S. Cl.
CPC ............. *G16H 30/20* (2018.01); *G06N 20/00* (2019.01)

(58) Field of Classification Search
CPC .......... G16H 30/20; G16H 30/40; G06N 20/00
See application file for complete search history.

(56) References Cited

U.S. PATENT DOCUMENTS

| | | | |
|---|---|---|---|
| 6,171,256 B1 | 1/2001 | Joo et al. | |
| 2008/0071182 A1 | 3/2008 | Cazares et al. | |
| 2018/0140203 A1 | 5/2018 | Wang et al. | |
| 2019/0259496 A1* | 8/2019 | Pemberton | A61B 5/318 |
| 2019/0313960 A1* | 10/2019 | Clifford | A61B 5/352 |

OTHER PUBLICATIONS

International Patent Office, International Search Report dated Nov. 6, 2020 in Application No. PCT/US 20/45348.

* cited by examiner

*Primary Examiner* — Thai Q Tran
*Assistant Examiner* — Jose M Mesa
(74) *Attorney, Agent, or Firm* — Sughrue Mion, PLLC

(57) ABSTRACT

A method of performing electrocardiography (ECG) analysis by at least one processor, the method including receiving ECG data that is from multiple leads; grouping the ECG data into groups of data; generating, from each group of data, a feature vector using a respective machine learning model; and performing ECG analysis using the feature vectors generated from each of the groups of data.

11 Claims, 5 Drawing Sheets

TRAINING FRAMEWORK FOR MULTI-GROUP ELECTROCARDIOGRAPHY (MG-ECG) ANALYSIS

BACKGROUND

An electrocardiography (ECG) exam is one of the most common medical procedures which can help doctors diagnose many heart diseases, including atrial fibrillation, myocardial infarction, and acute coronary syndrome (ACS). Annually, around 300 million ECGs are recorded. Conventional approaches for ECG analysis tend to use digital signal processing algorithms, such as wavelet transformations, to compute features from ECG signals. However, such approaches are not comprehensive, thus using them alone would not be sufficient to distinguish multiple types of heart arrhythmias. Recent approaches adopt deep neural networks, such as a convolutional neural network (CNN) and a recurrent neural network (RNN), and may achieve good accuracy for multi-class classification tasks based on ECG signals. However, most of the existing works can work with only single lead of ECG data, which cannot provide comprehensive information for heart beats.

SUMMARY

Current training frameworks for ECG data relies on single-lead signals and fails to considering the geometry properties of electrodes and leads. Some embodiments of the present disclosure accept multiple-lead signals, e.g. 12-lead as a setting, and apply multiple axis-specific feature extraction modules followed by finely-tuned analysis models to achieve multiple goals of ECG analysis, such as ECG monitoring and alarming, and computer-aided diagnosis.

According to embodiments, a method of performing electrocardiography (ECG) analysis by at least one processor includes receiving ECG data that is from multiple leads; grouping the ECG data into groups of data; generating, from each group of the groups of data, a feature vector using a respective machine learning model; and performing ECG analysis using the feature vectors generated from each of the groups of data.

According to embodiments, a device for performing electrocardiography (ECG) analysis comprises at least one memory configured to store computer program code and at least one processor configured to access said computer program code and operate as instructed by said computer program code. The computer program code includes grouping code configured to cause the at least one processor to group ECG data, that is from multiple leads and received by the at least one processor, into groups of data; generating code configured to cause the at least one processor to generate, from each group of the groups of data, a feature vector using a respective machine learning model stored in the at least one memory; and performing code configured to cause the at least one processor to perform ECG analysis using the feature vectors generated from each of the groups of data.

According to embodiments, a non-transitory computer-readable medium storing computer instructions that, when executed by at least one processor of a device, cause the at least one processor to receive electrocardiography (ECG) data that is from multiple leads; group the ECG data into groups of data; generate, from each group of the groups of data, a feature vector using a respective machine learning model stored in the memory; and perform ECG analysis using the feature vectors generated from each of the groups of data.

DETAILED DESCRIPTION

Some embodiments of the present disclosure are designed to achieve multiple data analysis tasks with both single-lead and multi-lead ECG data. In an embodiment, a multi-group electrocardiography (MG-ECG) analysis framework uses a grouping module which groups data streams from multiple ECG leads into groups based on different criteria. Two criteria may be, for example, (1) making all leads into a single group; (2) making each lead into a specific group. In an embodiment, a multi-axis feature extraction module adopts multiple models for each pre-defined groups from the grouping module, and the data features from multiple models are collected for the final analysis module. Therefore, an MG-ECG analysis framework of an embodiment can be widely applied to various types of analysis tasks. The MG-ECG analysis framework can also put background knowledge, such as geometry properties, ontologies, into account for analysis.

Figure 1:
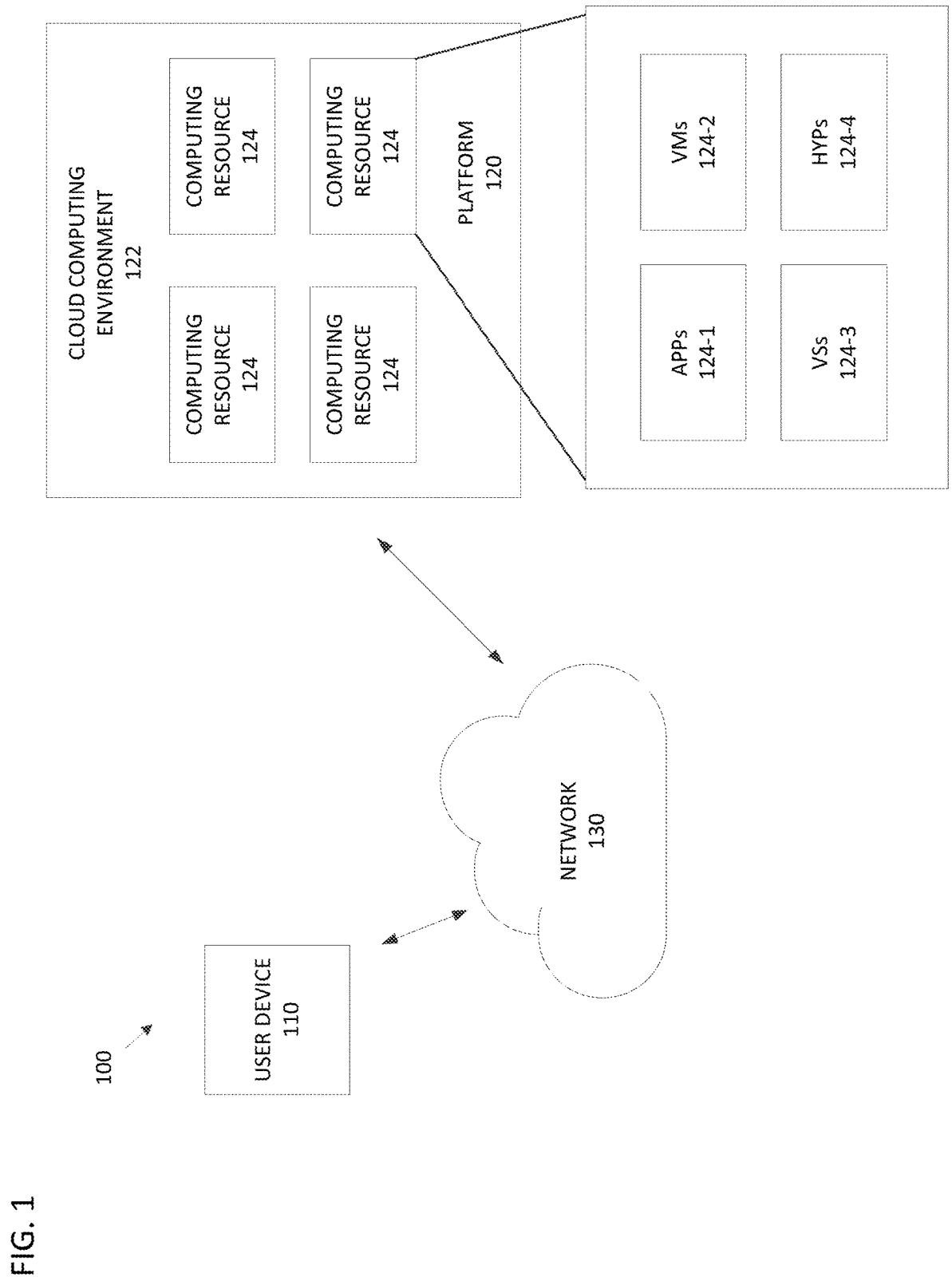
FIG. 1 is a diagram of an environment in which methods, apparatuses, and systems described herein may be implemented, according to embodiments.

FIG. 1 is a diagram of an environment 100 in which methods, apparatuses and systems described herein may be implemented, according to embodiments. As shown in FIG. 1, environment 100 may include a user device 110, a platform 120, and a network 130. Devices of environment 100 may interconnect via wired connections, wireless connections, or a combination of wired and wireless connections.

User device 110 includes one or more devices capable of receiving, generating, storing, processing, and/or providing information associated with platform 120. For example, user device 110 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 110 may receive information from and/or transmit information to platform 120.

Platform 120 includes one or more devices as described elsewhere herein. In some implementations, platform 120 may include a cloud server or a group of cloud servers. In some implementations, platform 120 may be designed to be modular such that software components may be swapped in or out depending on a particular need. As such, platform 120 may be easily and/or quickly reconfigured for different uses.

In some implementations, as shown, platform 120 may be hosted in cloud computing environment 122. Notably, while implementations described herein describe platform 120 as being hosted in cloud computing environment 122, in some implementations, platform 120 is not be cloud-based (i.e., may be implemented outside of a cloud computing environment) or may be partially cloud-based.

Cloud computing environment 122 includes an environment that hosts platform 120. Cloud computing environment 122 may provide computation, software, data access, storage, etc. services that do not require end-user (e.g., user device 110) knowledge of a physical location and configuration of system(s) and/or device(s) that hosts platform 120. As shown, cloud computing environment 122 may include a group of computing resources 124 (referred to collectively as "computing resources 124" and individually as "computing resource 124").

Computing resource 124 includes one or more personal computers, workstation computers, server devices, or other types of computation and/or communication devices. In some implementations, computing resource 124 may host platform 120. The cloud resources may include compute instances executing in computing resource 124, storage devices provided in computing resource 124, data transfer devices provided by computing resource 124, etc. In some implementations, computing resource 124 may communicate with other computing resources 124 via wired connections, wireless connections, or a combination of wired and wireless connections.

As further shown in FIG. 1, computing resource 124 includes a group of cloud resources, such as one or more applications ("APPs") 124-1, one or more virtual machines ("VMs") 124-2, virtualized storage ("VSs") 124-3, one or more hypervisors ("HYPs") 124-4, or the like.

Application 124-1 includes one or more software applications that may be provided to or accessed by user device 110 and/or platform 120. Application 124-1 may eliminate a need to install and execute the software applications on user device 110. For example, application 124-1 may include software associated with platform 120 and/or any other software capable of being provided via cloud computing environment 122. In some implementations, one application 124-1 may send/receive information to/from one or more other applications 124-1, via virtual machine 124-2.

Virtual machine 124-2 includes a software implementation of a machine (e.g., a computer) that executes programs like a physical machine. Virtual machine 124-2 may be either a system virtual machine or a process virtual machine, depending upon use and degree of correspondence to any real machine by virtual machine 124-2. A system virtual machine may provide a complete system platform that supports execution of a complete operating system ("OS"). A process virtual machine may execute a single program, and may support a single process. In some implementations, virtual machine 124-2 may execute on behalf of a user (e.g., user device 110), and may manage infrastructure of cloud computing environment 122, such as data management, synchronization, or long-duration data transfers.

Virtualized storage 124-3 includes one or more storage systems and/or one or more devices that use virtualization techniques within the storage systems or devices of computing resource 124. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 124-4 may provide hardware virtualization techniques that allow multiple operating systems (e.g., "guest operating systems") to execute concurrently on a host computer, such as computing resource 124. Hypervisor 124-4 may present a virtual operating platform to the guest operating systems, and may manage the execution of the guest operating systems. Multiple instances of a variety of operating systems may share virtualized hardware resources.

Network 130 includes one or more wired and/or wireless networks. For example, network 130 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of environment 100 may perform one or more functions described as being performed by another set of devices of environment 100.

Figure 2:
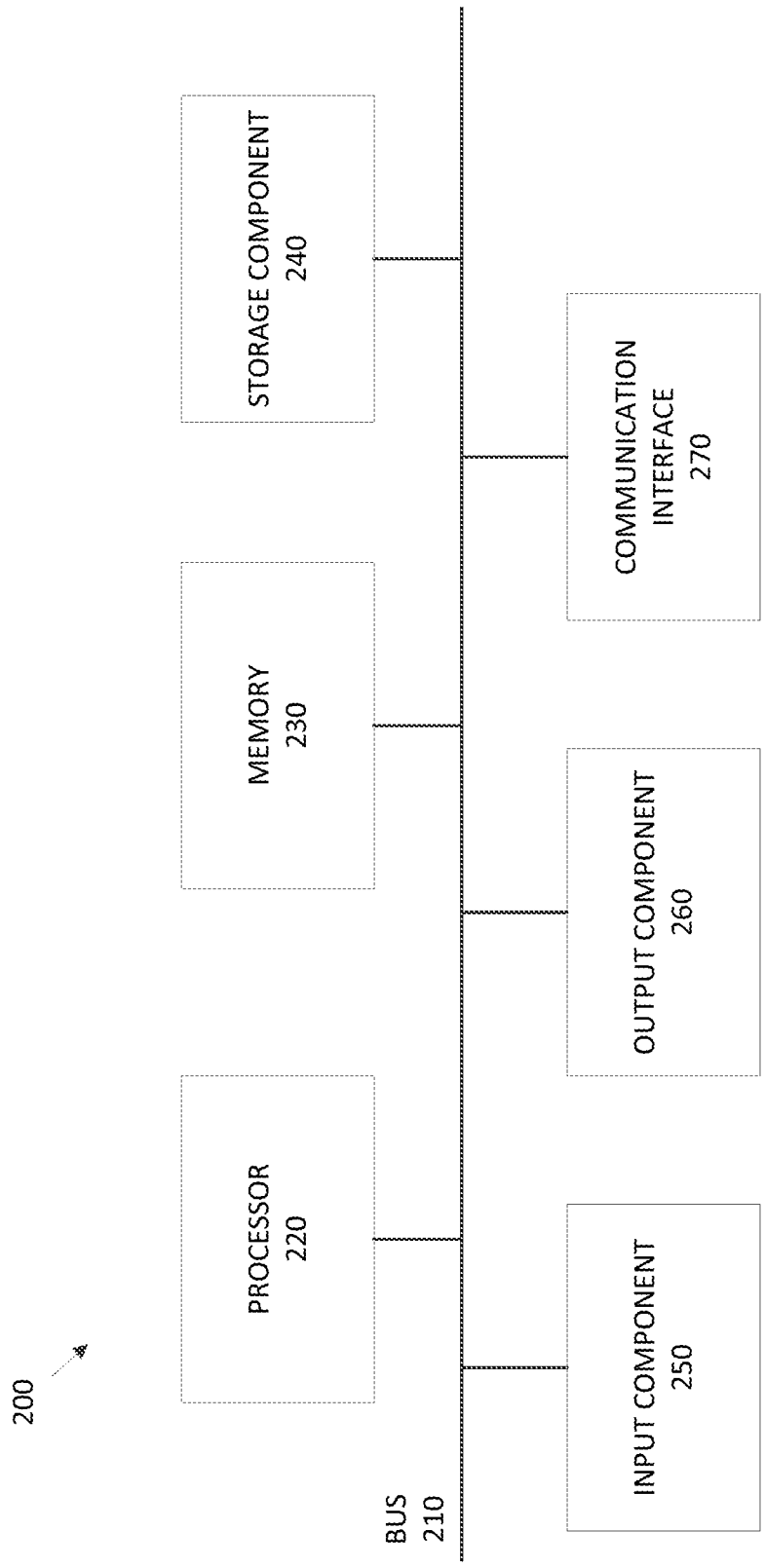
FIG. 2 is a diagram of example components of one or more devices of FIG. 1.

FIG. 2 is a diagram of example components of one or more devices of FIG. 1. A device 200 may correspond to user device 110 and/or platform 120. As shown in FIG. 2, device 200 may include a bus 210, a processor 220, a memory 230, a storage component 240, an input component 250, an output component 260, and a communication interface 270.

Bus 210 includes a component that permits communication among the components of device 200. Processor 220 is implemented in hardware, firmware, or a combination of hardware and software. Processor 220 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 220 includes one or more processors capable of being programmed to perform a function. Memory 230 includes a random access memory (RAM), a read only memory (ROM), and/or another type of dynamic or static storage device (e.g., a flash memory, a magnetic memory, and/or an optical memory) that stores information and/or instructions for use by processor 220.

Storage component 240 stores information and/or software related to the operation and use of device 200. For example, storage component 240 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 250 includes a component that permits device 200 to receive information, such as via user input (e.g., a touch screen display, a keyboard, a keypad, a mouse, a button, a switch, and/or a microphone). Additionally, or alternatively, input component 250 may include a sensor for sensing information (e.g., a global positioning system (GPS) component, an accelerometer, a gyroscope, and/or an actuator). Output component 260 includes a component that provides output information from device 200 (e.g., a display, a speaker, and/or one or more light-emitting diodes (LEDs)).

Communication interface 270 includes a transceiver-like component (e.g., a transceiver and/or a separate receiver and transmitter) that enables device 200 to communicate with other devices, such as via a wired connection, a wireless connection, or a combination of wired and wireless connections. Communication interface 270 may permit device 200 to receive information from another device and/or provide information to another device. For example, communication interface 270 may include an Ethernet interface, an optical interface, a coaxial interface, an infrared interface, a radio frequency (RF) interface, a universal serial bus (USB) interface, a Wi-Fi interface, a cellular network interface, or the like.

Device 200 may perform one or more processes described herein. Device 200 may perform these processes in response to processor 220 executing software instructions stored by a non-transitory computer-readable medium, such as memory 230 and/or storage component 240. A computer-readable medium is defined herein as a non-transitory memory device. A memory device includes memory space within a single physical storage device or memory space spread across multiple physical storage devices.

Software instructions may be read into memory 230 and/or storage component 240 from another computer-readable medium or from another device via communication interface 270. When executed, software instructions stored in memory 230 and/or storage component 240 may cause processor 220 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 2 are provided as an example. In practice, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
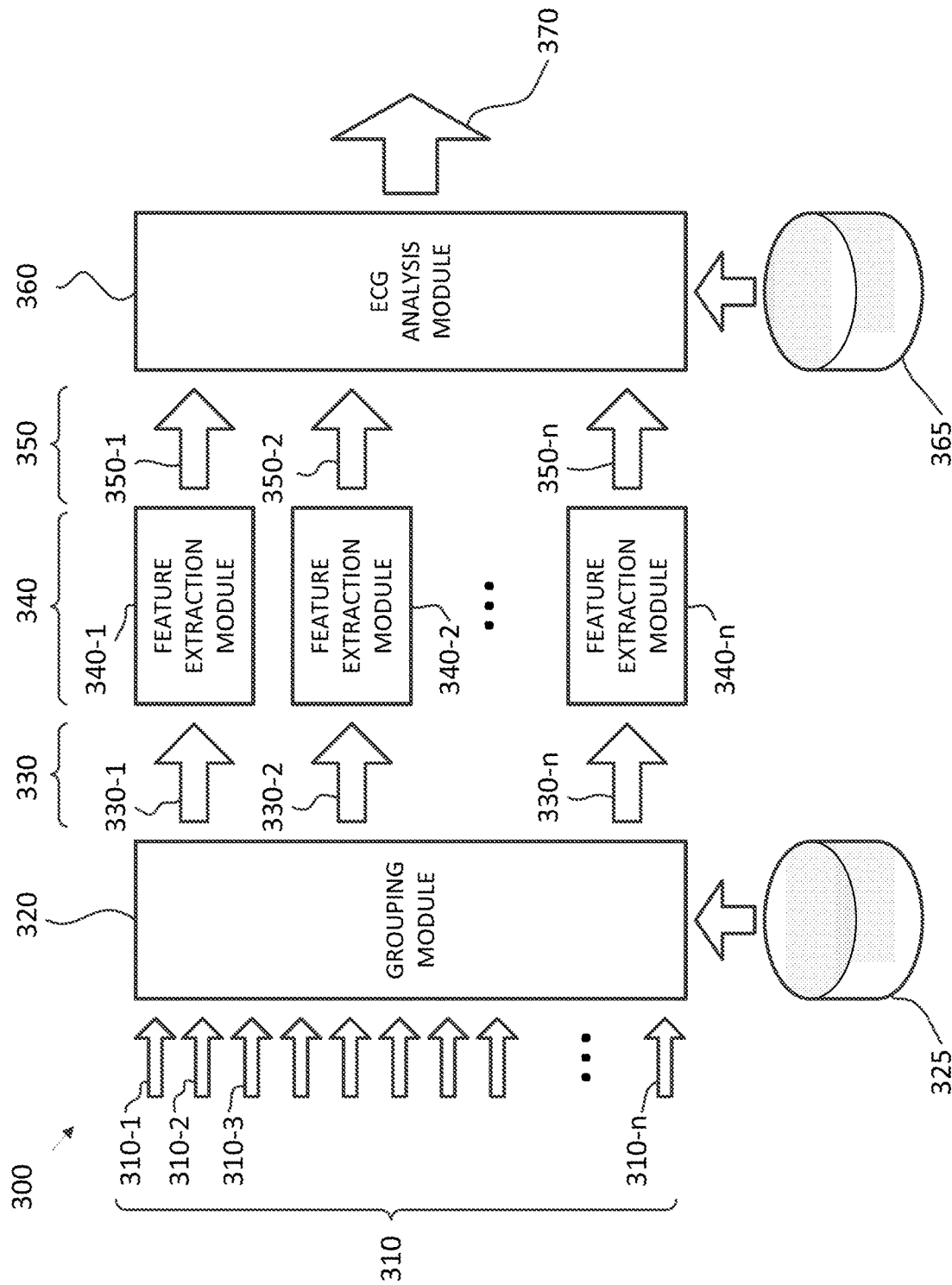
FIG. 3 is a diagram of a main architecture for an MG-ECG analysis framework of an embodiment.

FIG. 3 illustrates a main architecture for an MG-ECG analysis framework 300 of an embodiment.

The framework 300 may comprise three major modules: (1) a grouping module 320, (2) one or more feature extraction modules 340, and (3) an ECG analysis module 360. The grouping module 320 may group multi-lead ECG data into small groups. In an embodiment, a supportive grouping criteria pool 325 may provide different strategies that may help the grouping module 320 decide the group assignment. The feature extraction modules may each extract a group of ECG data with the same set of parameters. And the ECG analysis module 360 may finish a specific task such as clustering, classification, prediction, etc., and then achieve a final goal of the framework 300.

In an embodiment, the grouping module 320 may receive multiple ECG data 310 including, for example, ECG data 310-1, 310-2, ECG data 310-3, . . . , and ECG data 310-$n$, that are each from a respective lead. The grouping module 320 may receive the multiple ECG data 310 from, for example, an ECG device that includes multiple electrodes and leads for ECG examination. The grouping module 320 may group the multiple ECG data 310 into small groups 330. In an embodiment, the grouping module 320 may group the multiple ECG data 310 into groups 330-1, 330-2 . . . , and 330-$n$. In each group 330, the data share certain types of features or have common properties. The grouping module 320 may use a grouping criteria pool 325 or a set of built-in rules that are designed to decide how ECG data 310 are grouped. For example, supposing geometry properties of each lead of ECG data 310 are used as the criterion for grouping, the ECG data 300 from different leads may be grouped according to an electrodes' placement by assuming similar direction of ECG signals would provide similar features. The grouping module 320, especially the grouping criteria pool 325, may require domain knowledge and expert opinions to create rules and criteria for grouping. Several examples of criteria includes, but are not limited to, electrodes placement which defines the axis of ECG lead, contiguity of leads, and random grouping strategy. A preprocessing procedure for each group 330 of ECG data may be performed in the grouping module 320 to generate normalized and clean data observations.

In an embodiment, the framework 300 may include one or more feature extraction modules 340. For example, the framework 300 may include feature extraction modules 340-1, 340-2, . . . , 340-$n$. Grouped ECG data often share similar feature sets and common properties. Group-specified feature extraction modules 340 may be designed for a respective one of the data groups 330. For example, feature extraction module 340-1 may be designed for data group 330-1. In an embodiment, the feature extraction modules 340 may have similar structures so that the features extracted are comparable. The feature extraction modules 340 may accept pre-processed ECG data 330 as inputs, and generate feature vectors 350 as outputs. For example, the feature vectors 350 may include feature vectors 350-1, 350-2, . . . , and 350-$n$. Each of the feature vectors 350 may be, for example, a group of features. In an embodiment, each feature extraction module may output a respective one (or more) of the feature vectors 350. For example, feature extraction module 340-1 may output feature vector 350-1. Model-wise, the feature extraction modules 340 can use any machine learning approach(es), including, for example, support vector machine (SVM), random forests (RF), or deep learning models such as CNN and RNN. Each feature extraction module 340 may use a respective model(s). The parameters for each feature extraction module 340 may be trained separately to acquire a group-specified extraction approach.

The ECG analysis module 360 may accept extracted features and produce final outcomes 370 such as, for example, classification results, outlier alarms, predicted diagnosis including, for example, pathological signs. The outcomes 370 may be used in or include, for example, monitoring and alarming, computer-aided diagnosis, and detecting pathological signs. The ECG analysis module 360 may be provided with a task specific module pool 365. The task specific module pool 365 may be a collection of different models served for various ECG related tasks. For example, such models may include several statistical process control algorithms for ECG monitoring and alarming, several predictive models and classifier models for computer-aided diagnosis, and some statistical tools for general pathological status calculation. Depending on a goal of using the framework 300, the ECG analysis module 360 may deploy an appropriate tool from the task specific module pool 365 to finish the end-to-end framework and achieve a final goal.

At least one processor may be configured as the grouping module 320, the feature extraction modules 340, and the ECG analysis module 360 such that the at least one processor performs the functions of the modules. For example, a processor, or processors, of the at least one processor may together perform the functions of one or more of the modules, or a respective processor, or processors, of the at least one processor may perform the functions of each module.

Figure 4:
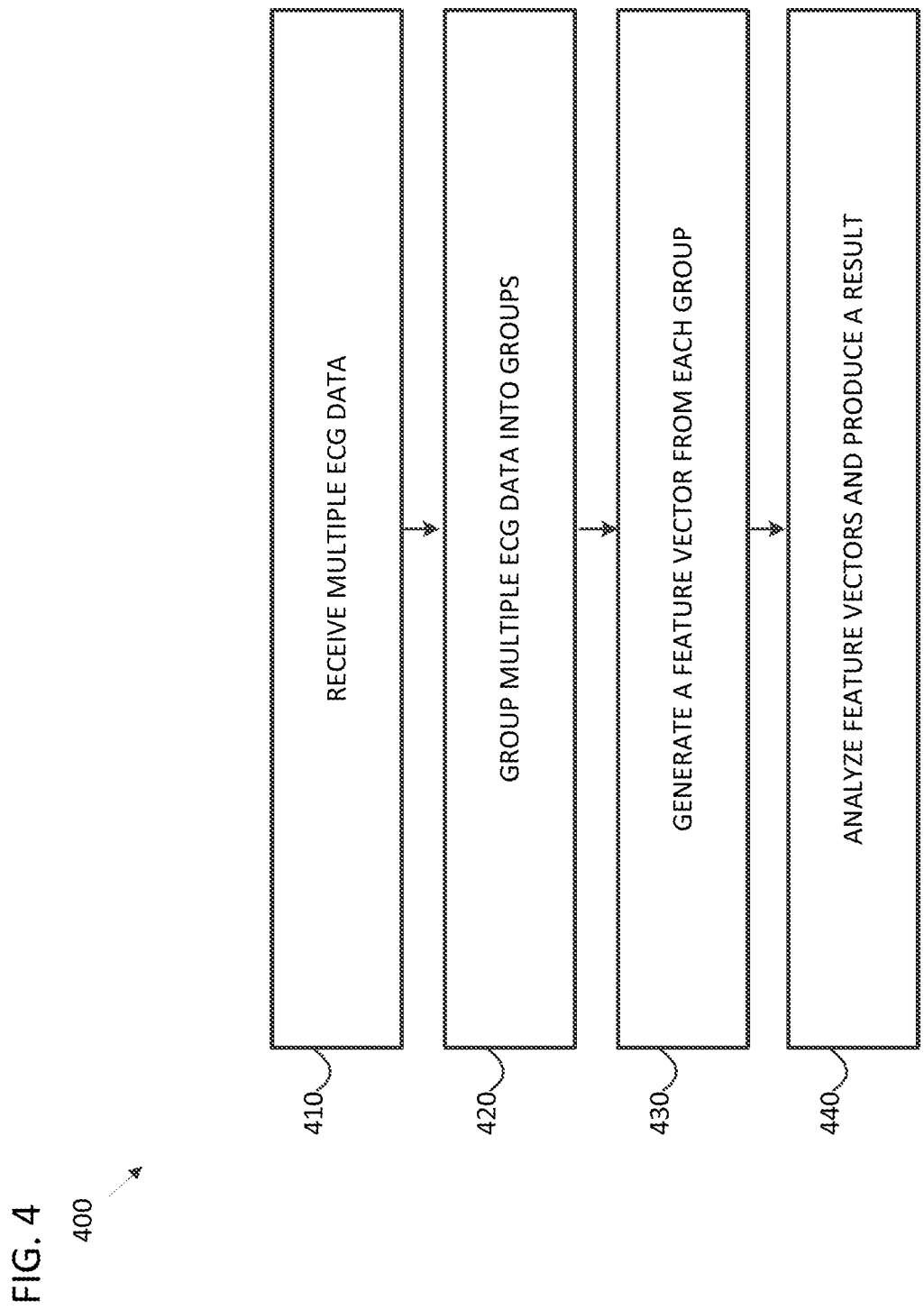
FIG. 4 is a flowchart of a method of performing ECG analysis, according to embodiments.

FIG. 4 illustrates a method performed by the at least one processor of an embodiment of the present disclosure.

In the embodiment, the at least one processor may receive multiple ECG data 310 (410). Following, the at least one processor may group the multiple ECG data 310 into groups 330 by performing the functions of the grouping module 320 (420). For example, in grouping the multiple ECG data 310, the at least one processor may use a supportive grouping criteria pool 325 that is stored within memory. Afterwards, the at least one processor may generate a feature vector 350 from each group 330 by performing the functions of each feature extraction module 340 (430). Then, the at least one processor may analyze the feature vectors 350 and produce a result 370 by performing the functions of the ECG analysis module 360 (440). For example, in analyzing the feature vectors 350, the at least one processor may use a task specific module pool 365 that is stored within one or more memory.

Figure 5:
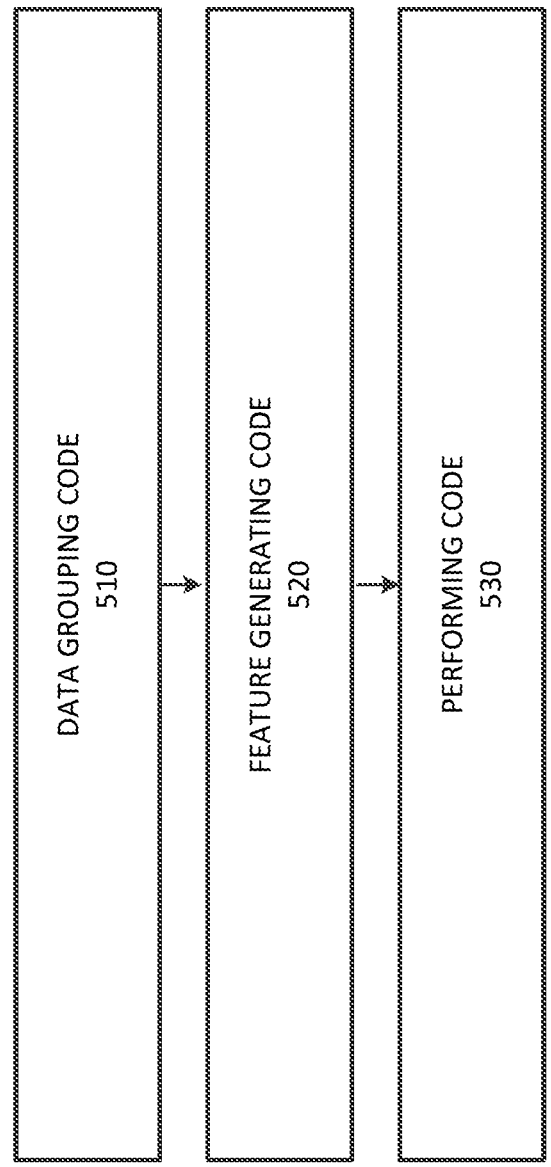
FIG. 5 is a diagram of an apparatus for performing an ECG analysis, according to embodiments.

FIG. 5 is a diagram of an apparatus 500 for performing ECG analysis, according to embodiments. As shown in FIG. 5, the apparatus 500 includes data grouping code 510, feature generating code 520, and performing code 540. The apparatus 500 may include at least one processor to perform one or more of the codes.

The data grouping code 510 may be configured to cause at least one processor to group the multiple ECG data 310 into groups 330 by causing the at least one processor to perform the functions of the grouping module 320. The feature generating code 520 may include multiple feature generating codes. Each of the multiple feature generating codes may be configured to cause at least one processor to generate a feature vector 350 from a respective group of groups 330 by causing the at least one processor to perform the functions of a respective feature extraction module 340. The performing code 530 may be configured to cause at least one processor to analyze the feature vectors 350 and produce a result 370 by causing the at least one processor to perform the functions of the ECG analysis module 360.

An embodiment of the present disclosure, such as the embodiment illustrated in FIG. 1, may be an end-to-end framework. An embodiment of the present disclosure is an improvement over existing approaches of ECG analysis model because, for example, the embodiment of the present disclosure may take the similarity as well as the differences of different leads into account by defining the extraction modules 340 with the same structure and includes a grouping module 320 that divides leads into small groups 330.

Moreover, an embodiment of the present disclosure may accept 12-lead ECG data which could provide comprehensive information for better performance of a model. Also, the grouping module of an embodiment may reduce the size of a whole model to enable applying the model on smaller devices such as laptops and mobile devices.

In an embodiment of the present disclosure, the grouping criterion, for the grouping module 320, could be loaded as built-in rules instead of a criteria pool. Such approach would be more efficient for specific tasks. In an embodiment of the present disclosure, the grouping results of the grouping module 320 could be either mutual exclusive groups or overlapped groups.

In an embodiment of the present disclosure, the feature extraction modules 340 could apply different types of models for different groups. Such approach would be a better choice for an overlapped grouping strategy. In an embodiment of the present disclosure, similar models of the feature extraction modules 340 could share a subset of parameters to account the similarity among groups.

Embodiments of the present disclosure may provide a framework that is designed as an end-to-end procedure such that the whole framework is optimized and altered simultaneously. An alternative, the procedure may be a step-by-step training procedure in which the feature extraction modules 340 can be trained separately, for instance, using an encoder and decoder structure.

Embodiments of the present disclosure are not limited to applications for ECG analysis. That is, embodiments of the present disclosure can be extended to other applications which have multiple sources of input.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method of performing electrocardiography (ECG) analysis training by at least one processor, the method comprising:
   receiving a plurality of pieces of ECG data, each of the plurality of pieces of ECG data including data from each of multiple leads;
   identifying common features in the plurality of pieces of ECG data;
   grouping individual pieces of the plurality of pieces of the ECG data into groups of data based on the identified common features, wherein the identified common features are based on a combination of a contiguity of the multiple leads and a random grouping strategy;
   generating, from each group of the groups of data, a feature vector using a respective machine learning model, wherein the respective machine learning model is used to generate the feature vector for a respective group of the groups of data, and wherein each of the respective machine learning models used has a group-specific extraction strategy based on the each of the respective machine learning models being a model trained separately; and
   performing ECG analysis using the feature vectors generated from each of the groups of data.

2. The method of claim 1, wherein the grouping further includes grouping the individual pieces of the plurality of pieces of the ECG data into the groups of data by using a grouping criteria pool or rules stored in memory.

3. The method of claim 2, wherein
   the grouping includes grouping the individual pieces of the plurality of pieces of the ECG data into the groups of data using the grouping criteria pool, and the identified common features include geometry properties of each of the multiple leads.

4. The method of claim 1, wherein the respective machine learning models used for each group of the groups of data have a same subset of parameters.

5. The method of claim 1, wherein the performing ECG analysis comprises:
   selecting a model from a plurality of models stored in memory; and
   generating an output using the feature vectors generated from each of the groups of data with the model.

6. A device for performing electrocardiography (ECG) analysis training, the device comprising:
   at least one memory configured to store computer program code;
   at least one processor configured to access said computer program code and operate as instructed by said computer program code, said computer program code including:
      receiving code configured to cause the at least one processor to receive a plurality of pieces of ECG data, each of the plurality of pieces of ECG data including data from each of multiple leads;
      identifying code configured to identify common features in the plurality of pieces of ECG data;
      grouping code configured to cause the at least one processor to group individual pieces of the plurality of pieces of the ECG data into groups of data based on the identified common features, wherein the identified common features are based on a combination of a contiguity of the multiple leads and a random grouping strategy;
      generating code configured to cause the at least one processor to generate, from each group of the groups of data, a feature vector using a respective machine learning model stored in the at least one memory, wherein the respective machine learning model is used to generate the feature vector for a respective group of the groups of data, and wherein each of the respective machine learning models used has a group-specific extraction strategy based on the each of the respective machine learning models being a model trained separately; and
      performing code configured to cause the at least one processor to perform ECG analysis using the feature vectors generated from each of the groups of data.

7. The device of claim 6, wherein the grouping code is configured to cause the at least one processor to group the individual pieces of the plurality of pieces of the ECG data into the groups of data by using a grouping criteria pool or rules stored in the at least one memory.

8. The device of claim 7, wherein the grouping code is configured to cause the at least one processor to group the individual pieces of the plurality of pieces of the ECG data into the groups of data by using the grouping criteria pool, and the identified common features include geometry properties of each of the multiple leads.

9. The device of claim 6, wherein the respective machine learning models used for each group of the groups of data have a same subset of parameters.

10. The device of claim 6, wherein the performing code comprises:
   model selecting code configured to cause the at least one processor to select a model from a plurality of models stored in the at least one memory; and
   output generating code configured to cause the at least one processor to generate an output using the feature vectors generated from each of the groups of data with the model.

11. A non-transitory computer-readable medium storing computer instructions that, when executed by at least one processor of a device, cause the at least one processor to:
   receive a plurality of pieces of ECG data, each of the plurality of pieces of ECG data including data from each of multiple leads;
   identifying common features in the plurality of pieces of ECG data;
   group individual pieces of the plurality of pieces of the ECG data into groups of data based on the identified common features, wherein the identified common features are based on a combination of a contiguity of the multiple leads and a random grouping strategy;
   generate, from each group of the groups of data, a feature vector using a respective machine learning model stored in a memory, wherein the respective machine learning model is used to generate the feature vector for a respective group of the groups of data, and wherein each of the respective machine learning models used has a group-specific extraction strategy based on the each of the respective machine learning models being a model trained separately; and
   perform ECG analysis using the feature vectors generated from each of the groups of data.

* * * * *